US00PP25214P2

(12) United States Plant Patent
Schaber

(10) Patent No.: US PP25,214 P2
(45) Date of Patent: Jan. 6, 2015

(54) GERANIUM PLANT NAMED 'OGLGER3012'

(50) Latin Name: *Pelargonium×domesticum*
Varietal Denomination: Oglger3012

(71) Applicant: Margaret Schaber, Encinitas, CA (US)

(72) Inventor: Margaret Schaber, Encinitas, CA (US)

(73) Assignee: Ecke Ranch B.V., De Lier (NL)

( * ) Notice: Subject to any disclaimer, the term of this patent is extended or adjusted under 35 U.S.C. 154(b) by 85 days.

(21) Appl. No.: 13/815,469

(22) Filed: Mar. 5, 2013

(51) Int. Cl.
*A01H 5/00* (2006.01)

(52) U.S. Cl.
USPC ..... Plt./331

(58) Field of Classification Search
USPC ..... Plt./331
See application file for complete search history.

*Primary Examiner* — Annette Para
(74) *Attorney, Agent, or Firm* — C. A. Whealy

(57) ABSTRACT

A new and distinct cultivar of Regal Geranium plant named 'Oglger3012', characterized by its upright to outwardly spreading and mounded plant habit; vigorous growth habit; freely branching habit; freely flowering habit; and large red purple, light red purple and white-colored flowers held above and beyond the foliar plane.

1 Drawing Sheet

Botanical designation: *Pelargonium×domesticum.*
Cultivar denomination: 'OGLGER3012'.

BACKGROUND OF THE INVENTION

The present invention relates to a new and distinct cultivar of Regal Geranium plant, botanically known as *Pelargonium×domesticum*, and hereinafter referred to by the name 'Oglger3012'.

The new Regal Geranium plant is a product of a planned breeding program conducted by the Inventor in Lompoc, Calif. The objective of the breeding program is to create new vigorous Regal Geranium plants with large and attractive flowers.

The new Regal Geranium plant originated from a cross-pollination made by the Inventor in December, 2001 in Lompoc, Calif. of a proprietary selection of *Pelargonium×domesticum* identified as code number 9977, not patented, as the female, or seed, parent with a proprietary selection of *Pelargonium×domesticum* identified as code number 8683, not patented, as the male, or pollen, parent. The new Regal Geranium plant was discovered and selected by the Inventor as a single flowering plant from within the progeny of the stated cross-pollination in a controlled greenhouse environment in Lompoc, Calif. in April, 2002.

Asexual reproduction of the new Regal Geranium plant by vegetative cuttings in a controlled greenhouse environment in Connellsville, Pa. since March, 2003 has shown that the unique features of this new Regal Geranium plant are stable and reproduced true to type in successive generations.

SUMMARY OF THE INVENTION

Plants of the new Regal Geranium have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Oglger3012'.

These characteristics in combination distinguish 'Oglger3012' as a new and distinct Regal Geranium plant:

1. Upright to outwardly spreading and mounded plant habit.
2. Vigorous growth habit.
3. Freely branching habit.
4. Freely flowering habit.
5. Large red purple, light red purple and white-colored flowers held above and beyond the foliar plane.

Plants of the new Regal Geranium differ primarily from plants of the female parent selection in flower color as plants of the female selection have pink-colored flowers.

Plants of the new Regal Geranium differ primarily from plants of the male parent selection in flower color as plants of the male selection have red-colored flowers.

Plants of the new Regal Geranium can be compared to plants of *Pelargonium×domesticum* 'Elegance Rose Bicolor', disclosed in U.S. Plant Pat. No. 13,492. In side-by-side comparisons conducted in Encinitas, Calif., plants of the new Regal Geranium differed primarily from plants of 'Elegance Rose Bicolor' in the following characteristics:

1. Plants of the new Regal Geranium were more vigorous than plants of 'Elegance Rose Bicolor'.
2. Plants of the new Regal Geranium had larger leaves than plants of 'Elegance Rose Bicolor'.
3. Plants of the new Regal Geranium and 'Elegance Rose Bicolor' differed in flower color as plants of 'Elegance Rose Bicolor' had red purple and white-colored flowers.

BRIEF DESCRIPTION OF THE PHOTOGRAPHS

The accompanying colored photographs illustrate the overall appearance of the new Regal Geranium plant showing the colors as true as it is reasonably possible to obtain in colored reproductions of this type. Colors in the photographs may differ slightly from the color values cited in the detailed botanical description which accurately describe the colors of the new Regal Geranium plant.

The photograph at the bottom of the sheet comprises a side perspective view of a typical flowering plant of 'Oglger3012' grown in a container.

The photograph at the top of the sheet is a close-up view of a typical flowering plant of 'Oglger3012'.

DETAILED BOTANICAL DESCRIPTION

The aforementioned photographs and following observations, measurements and values describe plants grown during the winter and early spring in 16.5-cm containers in a polyethylene-covered greenhouse in Encinitas, Calif. and under cultural conditions which closely approximate Regal Geranium commercial production. During the production of the plants, day temperatures averaged 24° C., night temperatures averaged 16° C. and light levels averaged 4,000 foot-candles. Plants were 17 weeks old when the photographs and the description were taken. In the detailed description, color references are made to The Royal Horticultural Society Colour Chart, 2007 Edition, except where general terms of ordinary dictionary significance are used.

Botanical classification: *Pelargonium×domesticum* 'Oglger3012'.

Parentage:

*Female, or seed, parent*.—Proprietary selection of *Pelargonium×domesticum* identified as code number 9977, not patented.

*Male or pollen parent*.—Proprietary selection of *Pelargonium×domesticum* identified as code number 8683, not patented.

Propagation:

*Type*.—By vegetative cuttings.

*Time to initiate roots, summer*.—About seven to ten days at soil temperatures of 23° C.

*Time to initiate roots, winter*.—About two weeks at soil temperatures of 23° C.

*Time to produce a rooted young plant, summer*.—About three to four weeks at soil temperatures of 23° C.

*Time to produce a rooted young plant, winter*.—About four to five weeks at soil temperatures of 19.5° C.

*Root description*.—Medium in thickness, fibrous; white in color.

*Rooting habit*.—Moderate branching; medium density.

Plant description:

*Plant and growth habit*.—Upright to outwardly spreading and mounding plant habit; vigorous growth habit.

*Branching habit*.—Freely branching habit with about eight primary lateral branches developing per plant, each primary lateral branch with two to three secondary lateral branches; dense and bushy appearance; pinching enhances lateral branch development.

*Plant height, to top of umbels*.—About 32 cm.

*Plant height, to top of foliar plane*.—About 27 cm.

*Plant diameter (spread)*.—About 38 cm.

*Lateral branches*.—Length: About 23 cm. Diameter: About 9 mm. Internode length: About 2.6 cm. Texture: Pubescent; minute. Strength: Strong. Color: Close to 146C.

Foliage description:

*Arrangement*.—Alternate; simple.

*Length*.—About 6.4 cm.

*Width*.—About 9.2 cm.

*Shape*.—Semi-circular; palmately lobed.

*Apex*.—Acuminate.

*Base*.—Roughly truncate.

*Margin*.—Bi-serrate.

*Venation pattern*.—Palmate, reticulate.

*Texture, upper and lower surfaces*.—Pubescent; minute.

*Color*.—Developing leaves, upper surface: Close to 137C. Developing leaves, lower surface: Close to 146B. Fully expanded leaves, upper surface: Close to 146A; venation, close to 146B; no discernable zonation pattern. Fully expanded leaves, lower surface: Close to 146B; venation, close to 147C.

*Petiole*.—Length: About 3.9 cm. Diameter: About 3.5 mm. Texture, upper and lower surfaces: Pubescent. Color, upper and lower surfaces: Close to 146C.

Flower description:

*Flower arrangement*.—Nearly round flowers arranged in hemispherical and somewhat loose umbels arising from apical leaf axils; umbels displayed above and beyond the foliar plane on strong peduncles; umbels upright and flowers face upright or outwardly.

*Fragrance*.—Faintly fragrant; sweet floral.

*Quantity of flowers*.—Freely flowering habit; about five open flowers per umbel and about 42 umbels per plant at one time.

*Flowering season*.—In California, flowering is continuous during the spring and summer.

*Flower longevity*.—Individual flowers last about two to three days on the plant; flowers not persistent.

*Umbel height*.—About 7.6 cm.

*Umbel diameter*.—About 12 cm.

*Flower diameter*.—About 6.6 cm by 7 cm.

*Flower depth (height)*.—About 4.6 cm.

*Flower buds*.—Length: About 3.8 cm. Diameter: About 1.6 cm. Shape: Oblong to slightly obovate. Color: Close to 85D tinted with close to 71B.

*Petals*.—Quantity per flower and arrangement: Typically five in a single whorl; two upper petals, two lateral petals and one lower petal. Length: Upper petals: About 4.8 cm. Lateral petals: About 4.6 cm. Lower petal: About 4.6 cm. Width: Upper petals: About 4.1 cm. Lateral petals: About 2.8 cm. Lower petal: About 3 cm. Shape, all petals: Broadly obovate. Apex, all petals: Rounded. Base, all petals: Acute. Margin, all petals: Entire, sinuate. Texture, all petals, upper and lower surfaces: Smooth, glabrous; velvety. Color: When opening, all petals, upper surface: Close to 72C; venation, close to 67A. When opening, all petals, lower surface: Close to 69C. Fully opened, upper petals, upper surface: Towards the margins, close to N74C; central fan-shaped blotch, close to 59A; towards the base, close to N74A; at the base, close to NN155D; venation, close to N74A; color does not fade with development. Fully opened, lateral and lower petals, upper surface: Towards the apex, close to N74C; at the base, close to NN155D; venation, close to N74A; color does not fade with development. Fully opened, all petals, lower surface: Close to 76C.

*Sepals*.—Quantity per flower: Typically five arranged in a single whorl. Length: About 2.4 cm. Width: About 5 mm. Shape: Elliptical. Apex: Acuminate; apices reflexed. Base: Truncate. Margin: Entire. Texture, upper surface: Smooth, glabrous. Texture, lower surface: Pubescent; minute. Color, upper surface: Close to 146C. Color, lower surface: Close to 146B.

*Peduncle* (*umbel stem*).—Length: About 7.2 cm. Diameter: About 3 mm. Angle: About 45° from stem axis. Strength: Strong. Texture: Pubescent; minute. Color: Close to 146B.

*Pedicel* (*individual flower stem*).—Length: About 2.4 cm. Diameter: About 2 mm. Angle: About 25° to 45° from peduncle axis. Strength: Strong. Texture: Pubescent; minute. Color: Close to 146C.

*Reproductive organs*.—Androecium: Stamen quantity per flower: About five. Filament length: About 1.4 cm. Filament color: Close to NN155D. Anther length: About 4 mm. Anther shape: Oblong. Anther color: Close to 64B. Pollen amount: Moderate. Pollen color: Close to 175B. Gynoecium: Pistil quantity per flower: One. Pistil length: About 1.9 cm. Stigma shape: Five-parted, star-shaped. Stigma color: Close to 187C. Style length: About 9 mm. Style color: Close to 64C. Ovary color: Close to 194A.

*Seeds and fruits*.—Seed and fruit development have not been observed on plants of the new Regal Geranium.

Disease & pest resistance: Plants of the new Regal Geranium have not been observed to be resistant to pathogens and pests common to Regal Geranium plants.

Temperature tolerance: Plants of the new Regal Geranium have been observed to tolerate temperatures ranging from about 1° C. to about 35° C.

It is claimed:

1. A new and distinct Regal Geranium plant named 'Oglger3012' as illustrated and described.

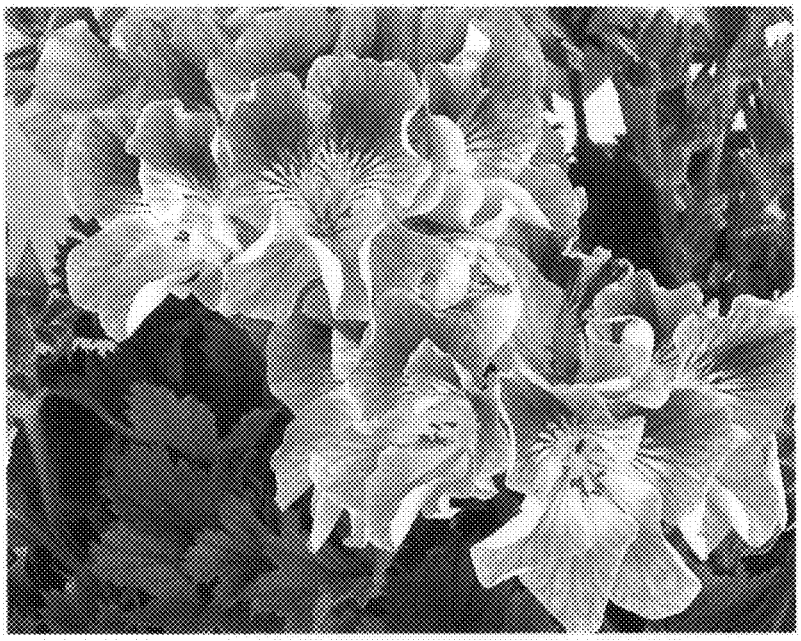
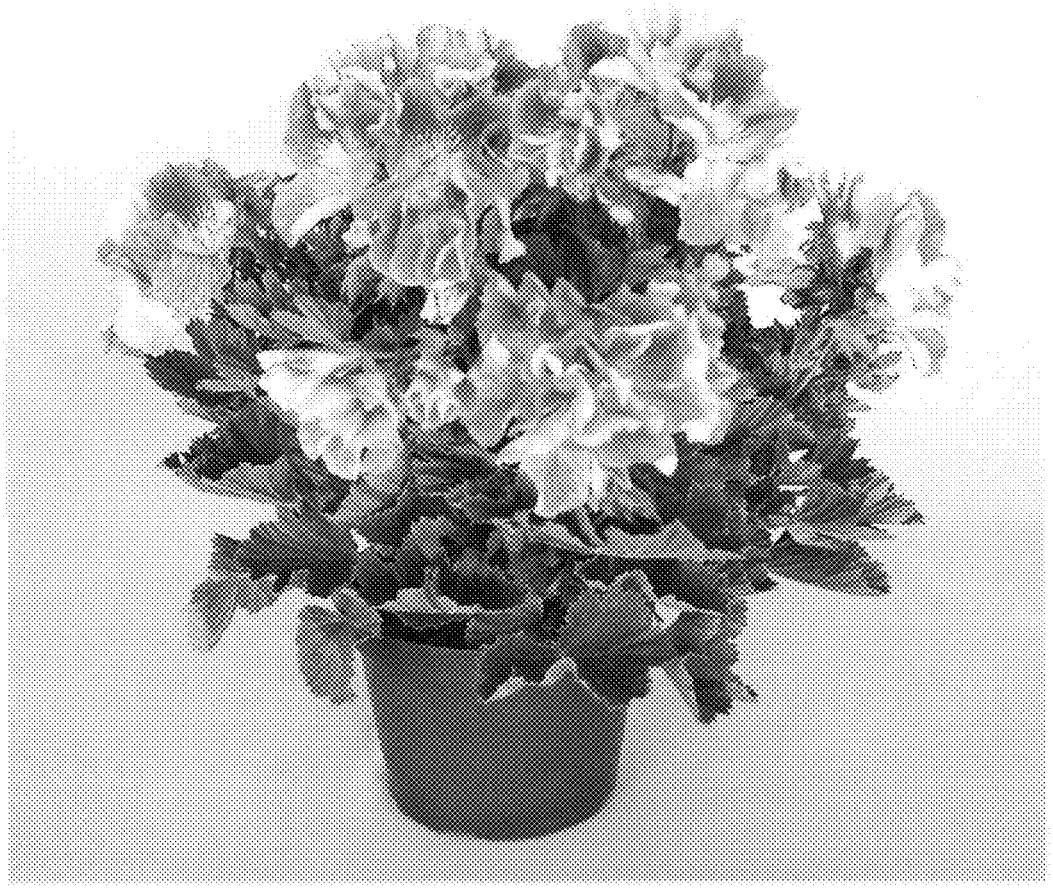

* * * * *